(12) United States Patent
Baker et al.

(10) Patent No.: US 11,666,708 B2
(45) Date of Patent: Jun. 6, 2023

(54) MEDICAMENT TRAINING DEVICE WITH PLUNGER LIMITING MECHANISM

(71) Applicant: NOBLE INTERNATIONAL, INC., Orlando, FL (US)

(72) Inventors: Jeff Baker, Orlando, FL (US); Tingting Liu, Orlando, FL (US); Matthew Palyo, Orlando, FL (US); Joseph Reynolds, Belle Isle, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 39 days.

(21) Appl. No.: 16/633,678

(22) PCT Filed: Jul. 24, 2018

(86) PCT No.: PCT/US2018/043520
§ 371 (c)(1),
(2) Date: Jan. 24, 2020

(87) PCT Pub. No.: WO2019/023252
PCT Pub. Date: Jan. 31, 2019

(65) Prior Publication Data
US 2021/0060257 A1    Mar. 4, 2021

Related U.S. Application Data

(60) Provisional application No. 62/536,280, filed on Jul. 24, 2017.

(51) Int. Cl.
*A61M 5/315*    (2006.01)

(52) U.S. Cl.
CPC .... *A61M 5/31501* (2013.01); *A61M 5/31511* (2013.01); *A61M 5/31565* (2013.01)

(58) Field of Classification Search
CPC .......... A61M 5/31501; A61M 5/31511; A61M 5/31565; A61M 5/31505;
(Continued)

(56) References Cited

U.S. PATENT DOCUMENTS

| | | | |
|---|---|---|---|
| 4,610,668 A | * | 9/1986 | Fleig ............... A61M 5/3156 604/208 |
| 5,304,138 A | | 4/1994 | Mercado |

(Continued)

OTHER PUBLICATIONS

PCT/US2018/043520; International Search Report and Written Opinion, dated Oct. 22, 2018; 15 pages.

*Primary Examiner* — Nathan R Price
*Assistant Examiner* — Justin L Zamory
(74) *Attorney, Agent, or Firm* — Timothy H. Van Dyke; Wolter, Van Dyke, Davis, PLLC

(57) ABSTRACT

Embodiments including an injection device having a housing with an outer surface, an inner surface, a proximal end and a distal end, and a defining a chamber extending between the proximal end and the distal end are provided herein. The device may include a plunger having a first end and a second end, the plunger being movable proximally and distally within the chamber of the housing, the plunger comprising a plunger rod extending from the first end to the second end of the plunger; and a plunger limiting mechanism configured to interface with the plunger rod, to limit the proximal movement of the plunger and prevent removal of the plunger from the housing.

4 Claims, 17 Drawing Sheets

(58) Field of Classification Search
CPC ......... A61M 2005/31508; A61M 2005/31506; A61M 2005/3139
See application file for complete search history.

(56) References Cited

U.S. PATENT DOCUMENTS

| | | | |
|---|---|---|---|
| 6,171,285 B1 | 1/2001 | Johnson | |
| 6,981,963 B2 * | 1/2006 | Barker | A61M 5/326 |
| | | | 604/243 |
| 9,770,559 B2 * | 9/2017 | Armstrong | A61M 5/3134 |
| 2005/0182370 A1 * | 8/2005 | Hato | A61M 5/31501 |
| | | | 604/213 |
| 2008/0167625 A1 * | 7/2008 | Earhart | B29C 59/007 |
| | | | 604/218 |
| 2010/0076370 A1 * | 3/2010 | Howlett | A61M 39/24 |
| | | | 604/65 |
| 2012/0316509 A1 * | 12/2012 | Kayser | A61M 5/31595 |
| | | | 604/210 |
| 2018/0200448 A1 * | 7/2018 | Caclin | A61M 5/31501 |

\* cited by examiner

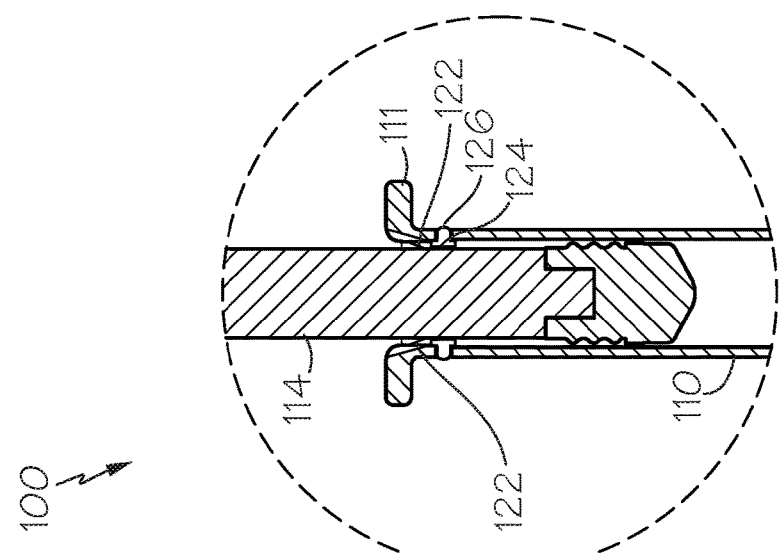
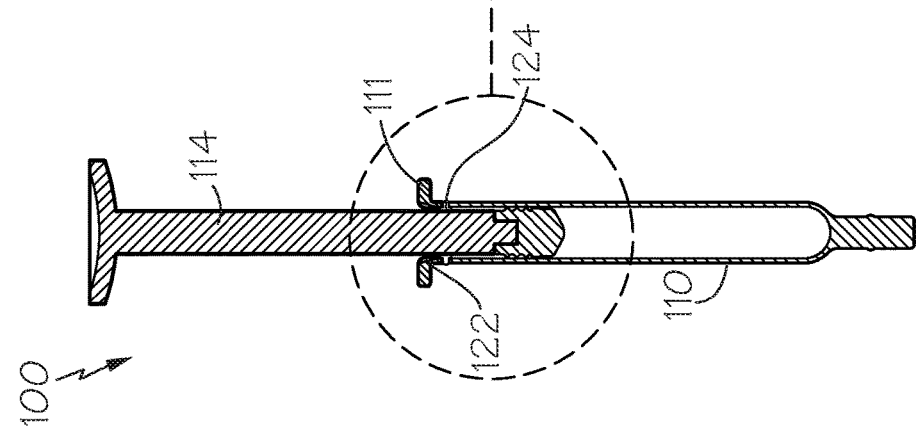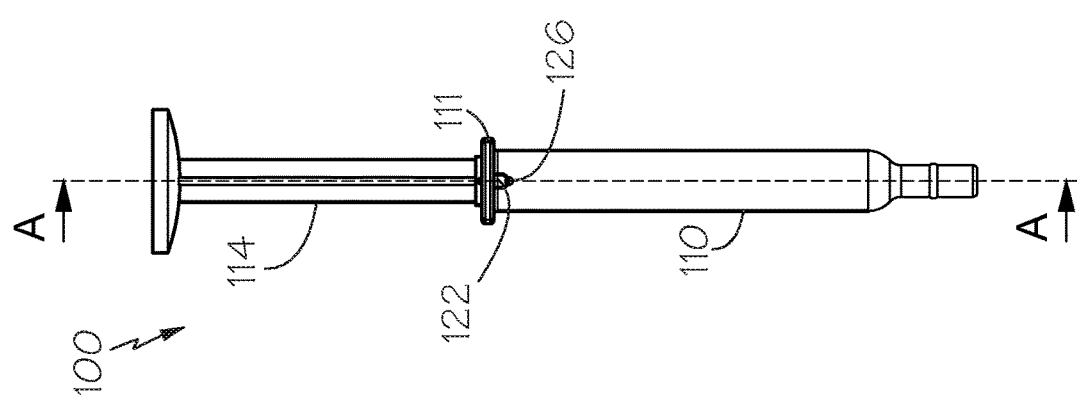
Fig. 5C
Fig. 5B
Fig. 5A

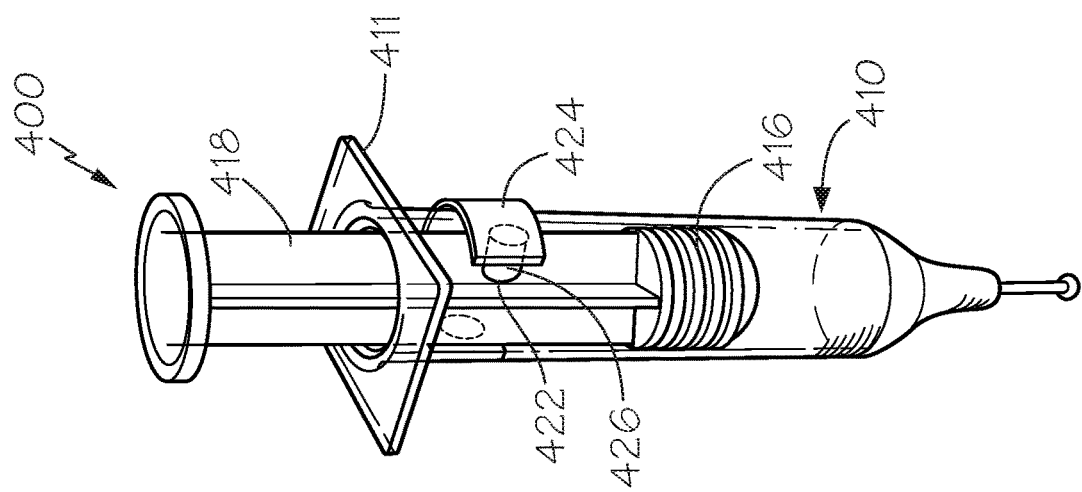
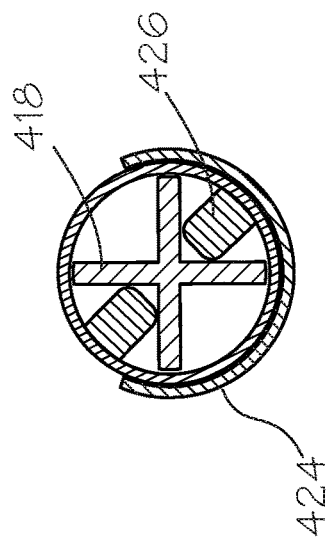
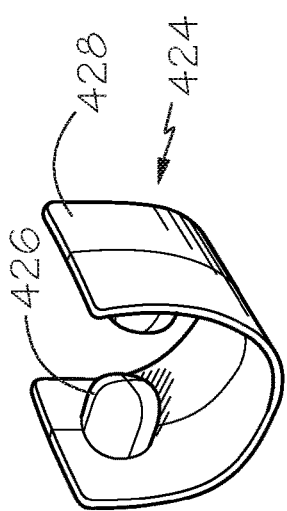
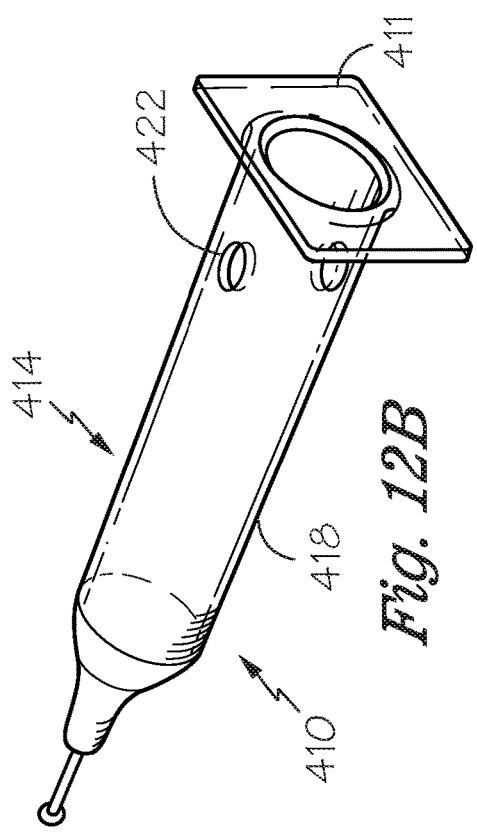
Fig. 12D
Fig. 12C
Fig. 12A
Fig. 12B

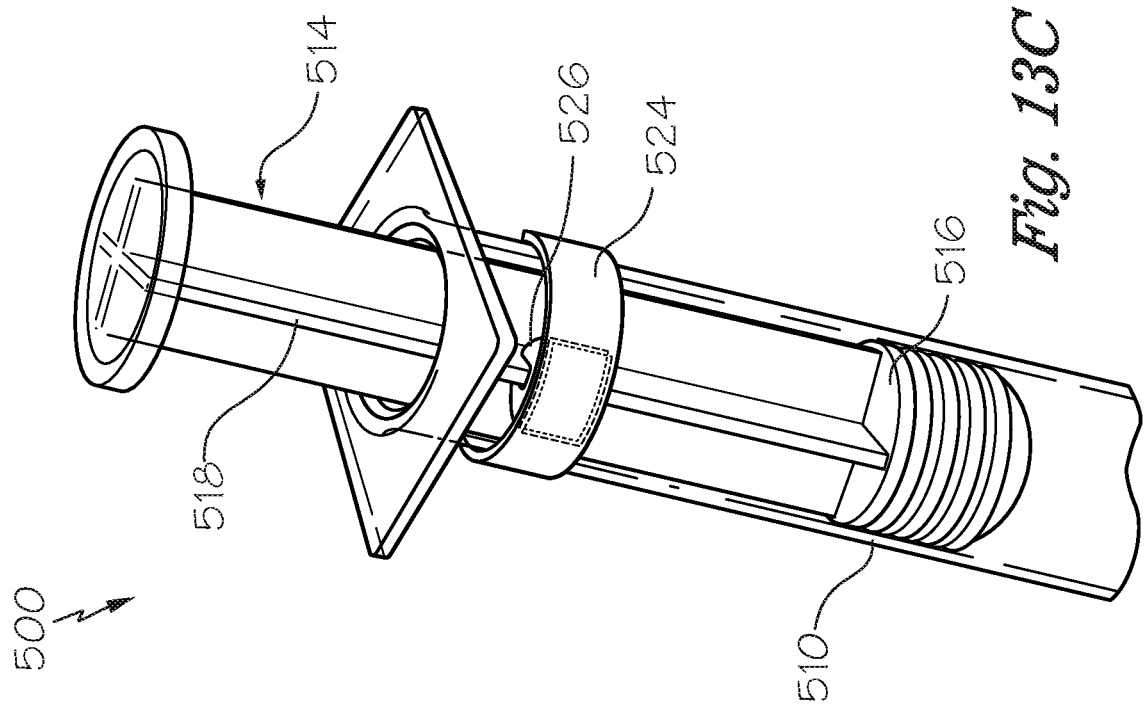
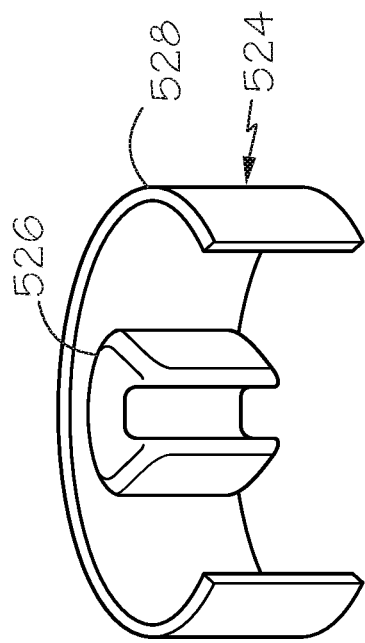
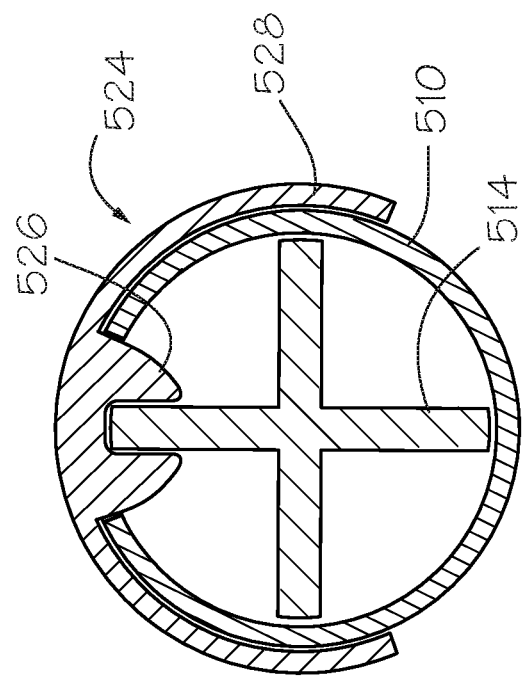

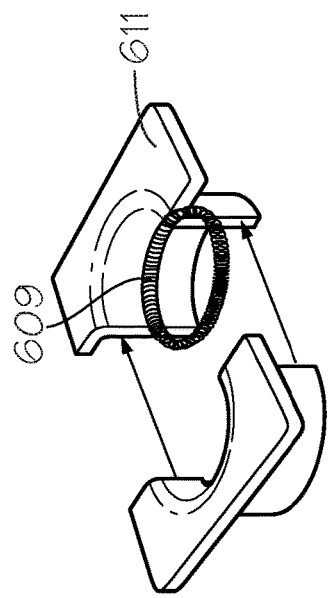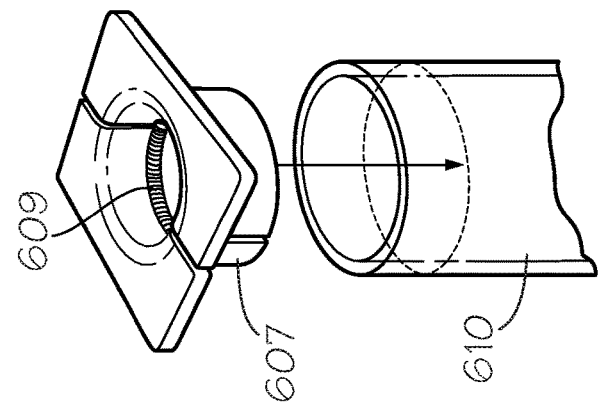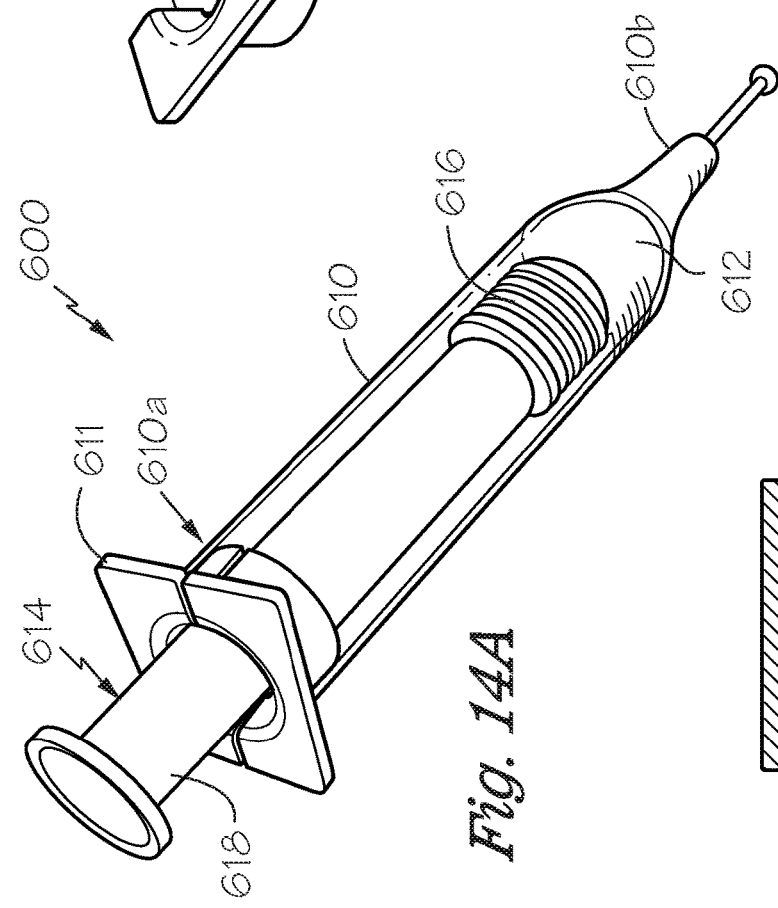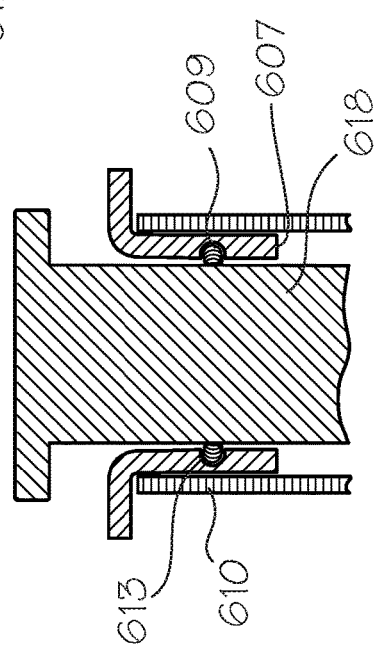
Fig. 14A
Fig. 14B
Fig. 14C
Fig. 14D

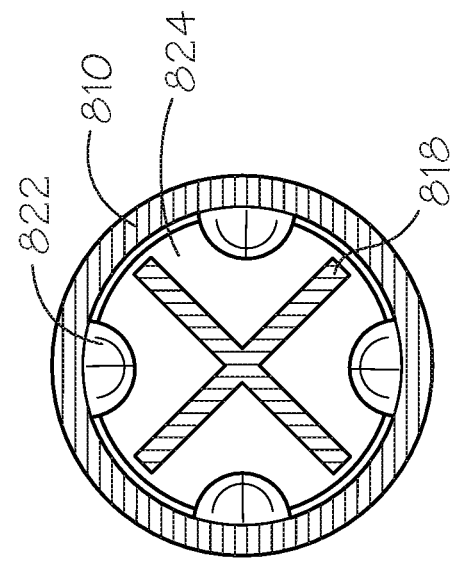
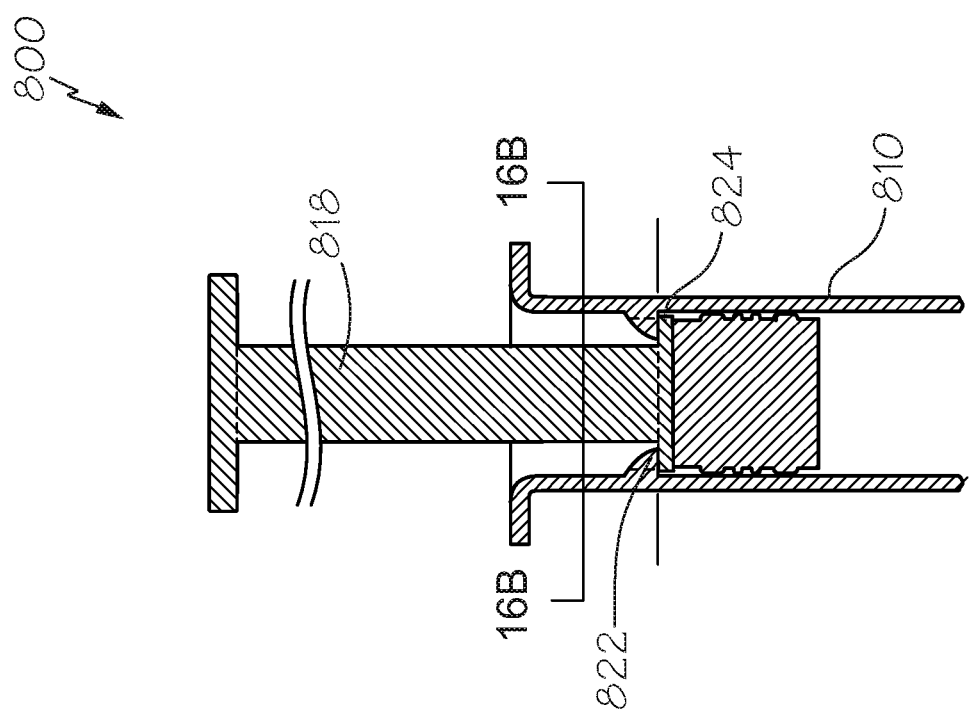
Fig. 16A
Fig. 16B

US 11,666,708 B2

MEDICAMENT TRAINING DEVICE WITH PLUNGER LIMITING MECHANISM

BACKGROUND

Performing a medical treatment or test on oneself carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self-administering medical treatment, as well as increasing efficacy and accuracy in providing the treatment to patients. Medical devices can be intimidating to use; the fear associated with giving oneself an injection, for example, can be traumatic. This fear is increased in persons with little or no experience in self-administration of medications. Consequently, devices and methods to assist in training individuals to inject themselves or otherwise self-administer medication are beneficial in decreasing or preventing the anxiety associated with medicament delivery.

SUMMARY

In embodiments herein, an injection device is provided. One injection device embodiment includes a housing including an outer surface, an inner surface, a proximal end and a distal end, and defining a chamber extending between the proximal end and the distal end. The injection device further includes a plunger having a first end and a second end, the plunger being movable proximally and distally within the chamber of the housing, the plunger comprising a plunger rod extending from the first end to the second end of the plunger, and a plunger limiting mechanism configured to interface with the plunger rod, to limit the proximal movement of the plunger and prevent removal of the plunger from the housing.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 5A is a side view of a medicament training device embodiment post insertion of the disc member into the device housing.

FIG. 5B is a cross sectional view taken at B-B of FIG. 5A.

FIG. 5C is a zoomed in view of a portion of the device embodiment shown in FIG. 5B.

FIGS. 12A-12D include perspective views of a clip embodiment, and of a device housing embodiment, and a top cross-sectional view of the device housing, and a perspective side view of the medicament delivery device (FIG. 12D).

FIG. 13A-C include perspective views of another clip embodiment, and a perspective view of a portion of a medicament training device embodiment (FIG. 13C), and a cross sectional top view of the device embodiment shown in FIG. 13C (FIG. 13B).

FIGS. 14A-D include a perspective view of a further medicament device embodiment (A), a cross sectional view of the device embodiment shown in FIG. 14A (B), a perspective view of a disassembled flange portion (C), and a partially assembled view of the flange shown in FIG. 14C and device housing (D).

FIG. 16A is a cross-sectional view of a device embodiment.

FIG. 16B is a cross-section of the device embodiment shown in FIG. 16A.

DETAILED DESCRIPTION

Figure 1:
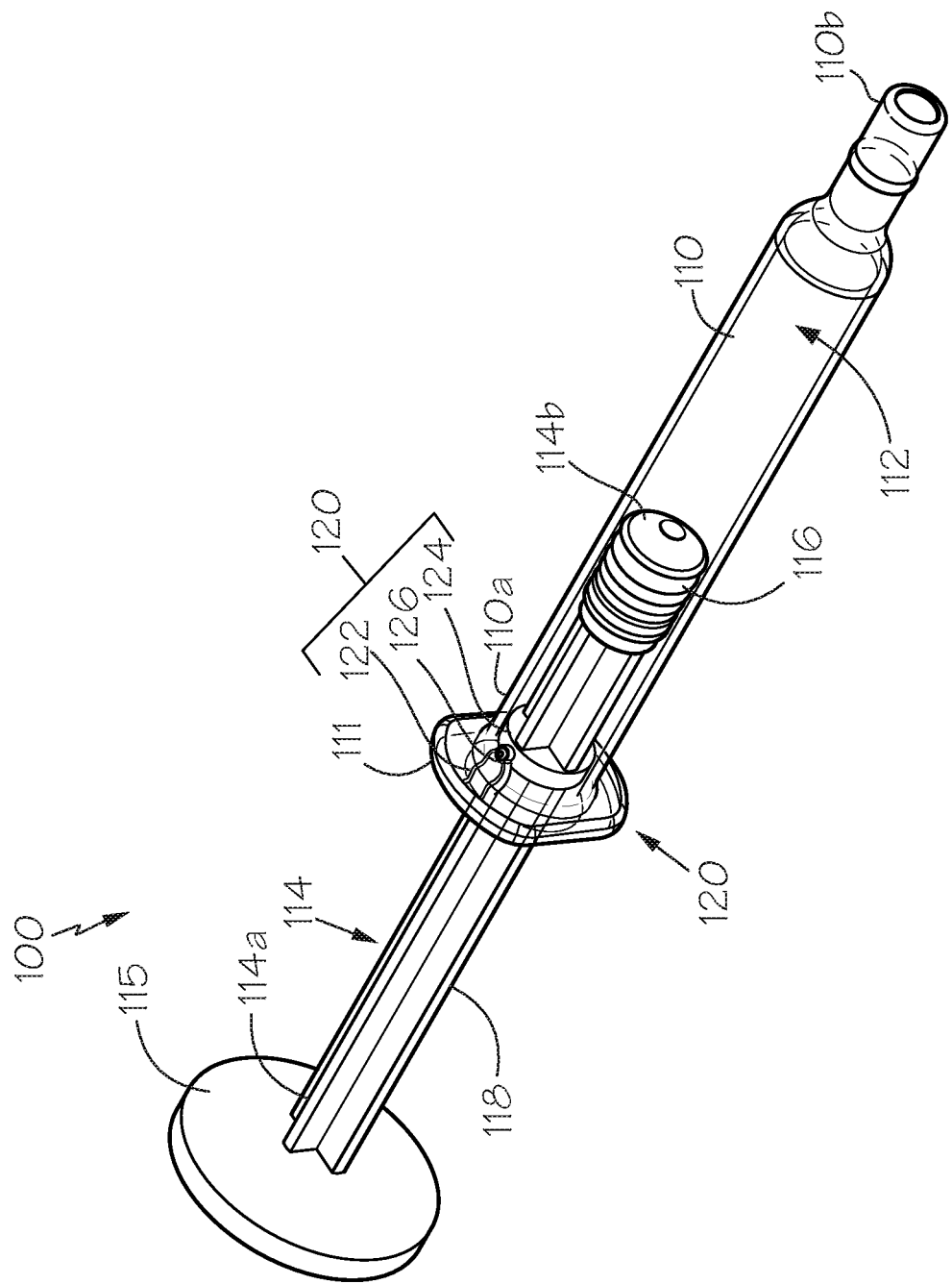
FIG. 1 is a perspective view of a medicament training device embodiment.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

The inventors have identified herein, a need for a training device to improve user confidence in self-delivery or self-administration of medicament, and to increase accuracy in medicament delivery device use. Moreover, inventors have found importance in simulating an injection device with a training device that may prevent removal of the plunger from the housing, as well as provide resettability of the plunger to a predefined position in the housing. The predefined position may include a proximal end of the housing, such that the distal end of the plunger can be reset to the most proximal end of the housing. In another embodiment, however, a predetermined reset or refill line is established in the training device. This reset or refill line may be used to mimic the reset or refill-line of the medicament delivery device. This will allow the trainer to train a user to reset the plunger to the reset or refill line following a use of the training device, and prior to a subsequent use, and prevent the user from resetting the plunger past the reset or refill-line. A number of embodiments described herein may provide plunger reset limitation, so as to guide a user as to how far to reset the plunger during use of the training device.

Exemplary embodiments of the medicament delivery training device can be implemented to educate users on the proper operation and usage of a medicament delivery device. The training device can be used to make prospective and current users of medicament delivery devices feel more comfortable and confident in self-administration of medicaments, and can help users understand the proper use of a medicament delivery device. Exemplary embodiments of the medicament delivery training device can be used by a user before the user administers an injection using a medicament delivery injection device and/or can be used as needed or desired by the user.

In some embodiments provided herein, a catch member limiting proximal movement of the plunger within the device housing may be provided. This form of somatic stimuli is provided to train a user 1) the distance to withdraw, or proximally move the plunger within the housing when using a medicament delivery device, by restricting movement of the plunger in the training device, and/or 2) not to remove the plunger from the housing of the medicament delivery device, by preventing removal of the plunger in the training device in a number of different ways.

The term associated or association, as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output.

As used herein, the terms "subject", "user" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

The term "injection device" as used herein may include training devices, including those which contain medicament and those which do not contain medicament. "Injection device" as used herein may also include non-training medicament-containing injection devices.

Various embodiments of a medicament training device used to limit or train limiting the proximal movement of a plunger within a device housing are provided and described in greater detail herein. One embodiment of an injection device 100 shown in a perspective view in FIG. 1, includes a device housing 110 having a proximal end 110a, a distal end 110b, wherein in some instances a housing flange 111 is disposed near the proximal end 110a, wherein the distal end 110b is configured to associate with a target location of a user. The housing 110 defines a chamber 112, wherein a plunger 114 is slidable between the proximal end 110a and the distal end 110b of the housing 110 within the chamber 112. In some embodiments, the plunger 114 may include a stopper 116 at or near its distal end 114b and a plunger flange 115 near its proximal end 114a. The plunger may include a plunger rod 118, extending between the proximal end 114a and the distal end 114b of the plunger 114. The plunger rod 118 may include a number of different profiles. In one embodiment, for example, the plunger rod 118 includes a cross profile as shown in FIG. 1. In other embodiments, the plunger rod 118 may include a cylindrical profile as shown in FIG. 14. Other profiles for the plunger rod 118 may exist, including, but not limited to a pyramidal profile, a square profile, among others. The length, shape, and surface texture of the plunger rod 118 may also be altered in a number of ways.

In the embodiment 100 shown in FIG. 1, a plunger limiting mechanism 120 is provided, including one or more tabs 122 provided on a portion of the housing. In the non-limiting embodiment of FIG. 1, the tabs 122 extend from an inner surface of the housing flange 111. The tabs 122 may alternatively extend from an inner portion of the housing 110, at any location between the proximal and distal ends of the housing 110a, 110b, in other non-limiting embodiments. Another portion of the plunger limiting mechanism 120 may include a feature of or on the plunger 114. This feature may include a protrusion 126, in one non-limiting embodiment. In the non-limiting embodiment shown in FIG. 1, the feature comprises a disc member 124. The disc member 124 is disposed on the plunger rod 118. The disc member 124 includes a protrusion 126 for interfacing with the tab 122 on the housing 110, when the plunger 114 is moved in a proximal direction, to limit proximal movement of the plunger 114 during resetting of the device 100. This plunger feature may be positioned at any location on the plunger rod. In an embodiment, the disc member may be fixed in a predetermined position on the plunger 114, wherein in a nonlimiting embodiment, the predetermined position may include a position simulating the position a user must draw the plunger back to in an injection device containing medicament in order to achieve an effective dose. The position may also be known as a medicament reset or refill-line. In some non-limiting embodiments, the position of the feature may be adjustable in order to adjust the training device to train a user for various medicaments or various dosages, such that the plunger 114 can be reset to the reset or refill-line specific to a particular dosage. The particular dosage may be medicament-specific, or patient-specific, in non-limiting embodiments.

Figure 2:
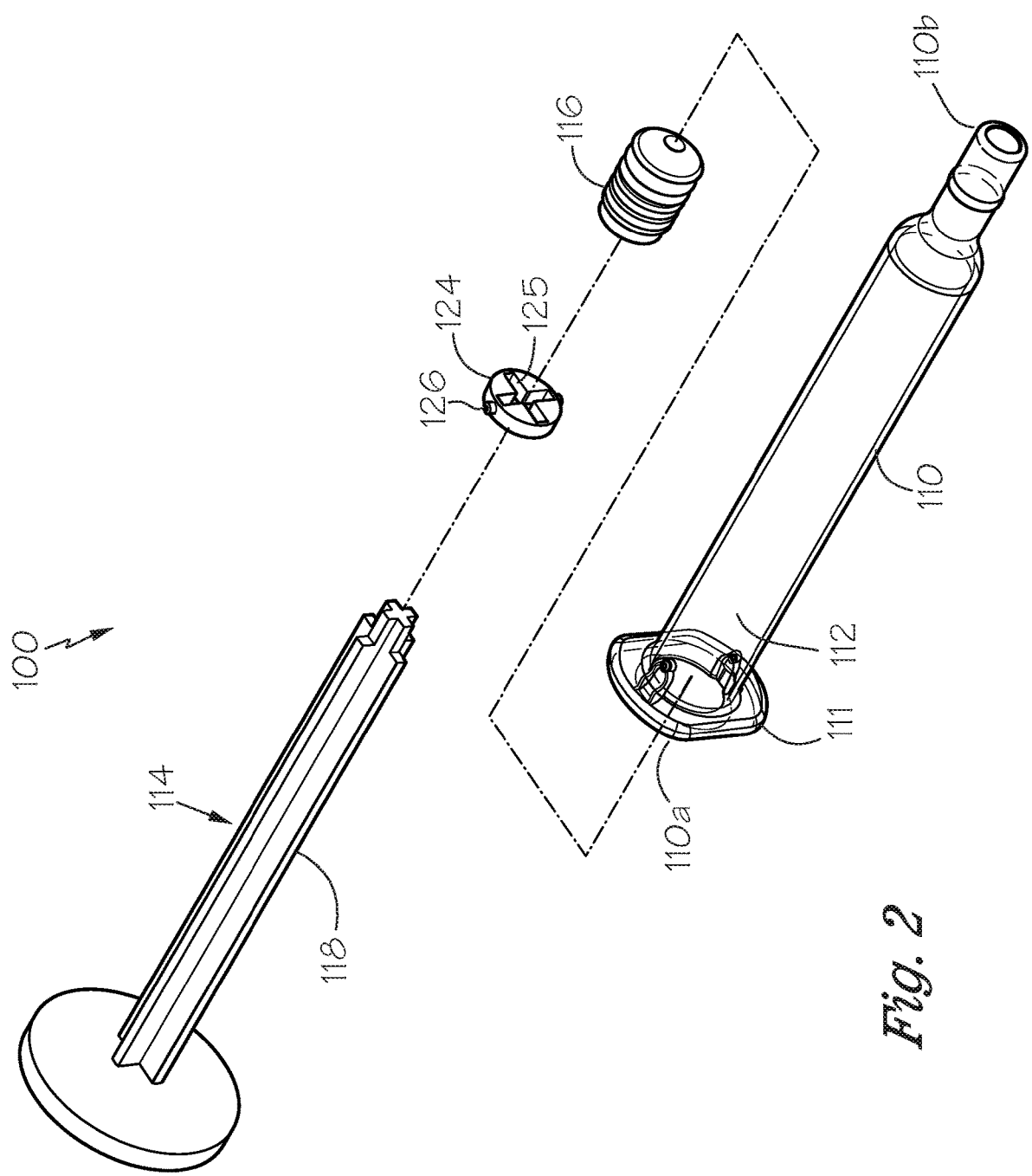
FIG. 2 is an exploded view of the embodiment shown in FIG. 1.

FIG. 2 provides an exploded view of the device embodiment 100 shown in FIG. 1. The exploded view shows the disc member 124, having the protrusion 126 disposed on its surface. In the device embodiment 100 shown in FIG. 2, the plunger rod 118 includes a cross-shaped profile, and consequently, the center of the disc member 124 includes a cross-shaped opening 125 to receive the plunger rod 118. In other non-limiting embodiments, the plunger rod 118 may include a different profile along its length, such as a cylindrically shaped rod as described above, and the disc member may include an opening corresponding to the shape of the plunger rod 118. In further embodiments, the profile of the plunger rod 118 may change along its length. The disc member 124 may be slid onto the plunger rod 118 and may be adjustable with respect to location along the length of the plunger rod 118 to set the reset position of the plunger 114.

Figure 3:
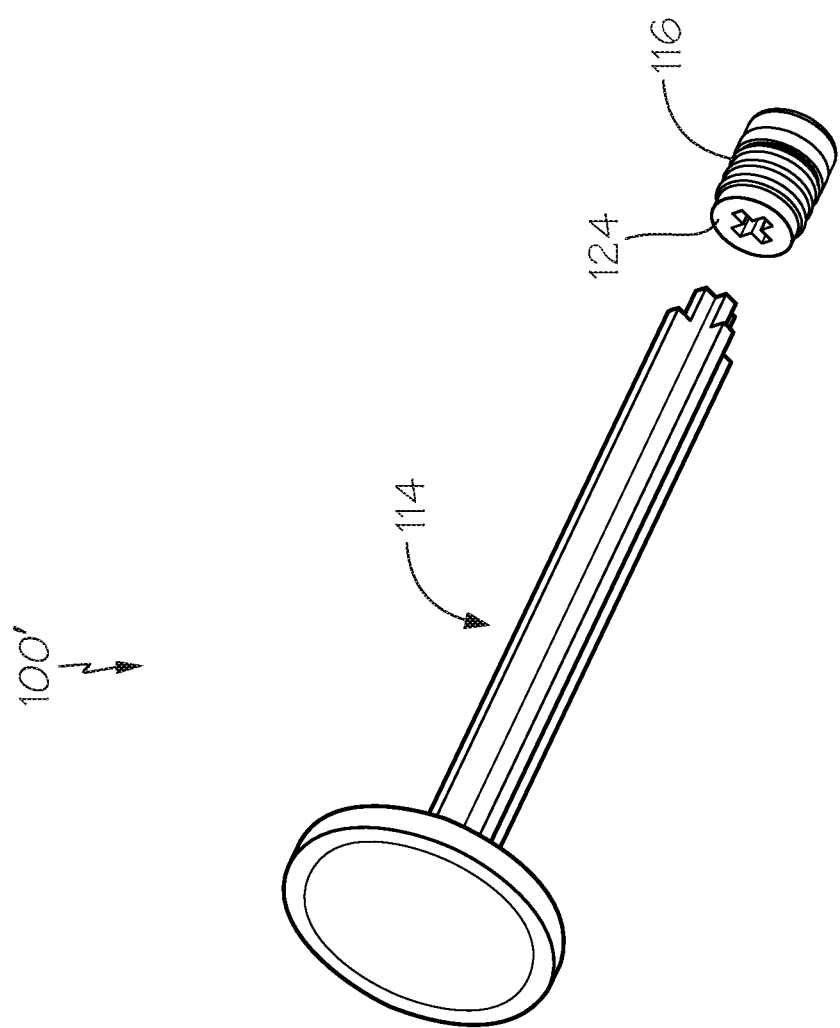
FIG. 3 is a perspective view of a plunger embodiment.

FIG. 3 shows a perspective view of an embodiment 100' including a plunger rod 114 as in FIGS. 1-2 and a stopper 116 attached to or associated with a disc member 124 to demonstrate that these components may be pre-attached or affixed to one another, removably or permanently, in varying embodiments. Furthermore, as shown in FIG. 3, the disc member 124 may be configured to remain associated with the stopper 116 at the distal end of the plunger 114, therefore the cross-shaped opening in the disc member 124 may correspond only to the smaller width of the cross-shaped portion of the distal end of the plunger rod 114.

Figure 4A:
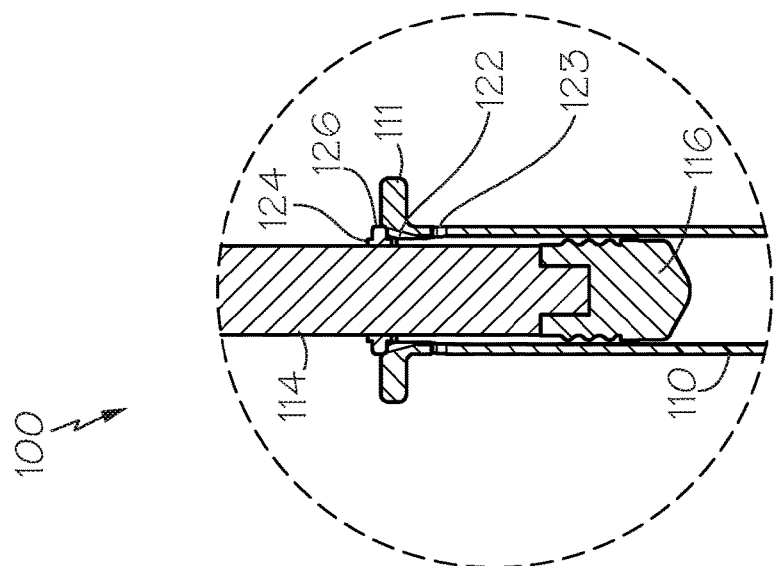
FIG. 4A is a side view of a medicament training device embodiment before insertion of a disc member into a housing.
Figure 4B:
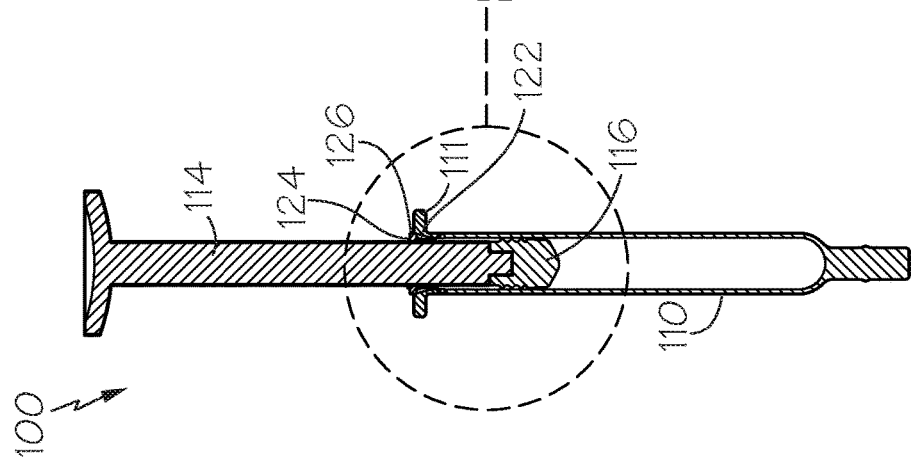
FIG. 4B is a cross sectional view taken at A-A of FIG. 4A.
Figure 4C:
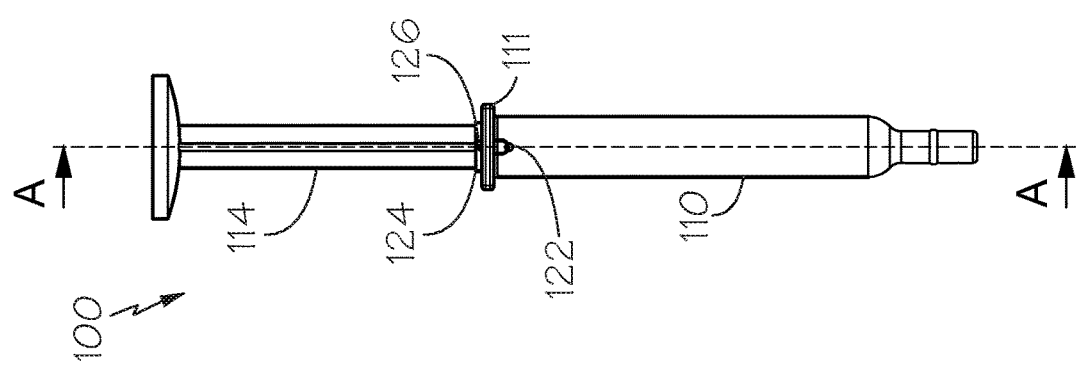
FIG. 4C is a zoomed in view of a portion of the device embodiment shown in FIG. 4B.

FIG. 4A includes a side view of the embodiment 100 of the device 100. FIG. 4B includes a cross-sectional view of the embodiment 100 as shown in FIG. 4A, taken at A-A. FIG. 4C is a zoomed in view of a portion of the device 100 outlined in FIG. 4B. FIGS. 4A-C show the plunger 114 having the disc member 124 disposed thereon prior to full insertion of the plunger 114. The disc member 124 with protrusion 126 can be seen in FIGS. 4A-C proximal to the housing flange 111. In the view of FIG. 4C, the tabs 122 are visible. In a non-limiting embodiment, the device housing 110 may include a notch 123 as shown in FIG. 4C.

The notch 123 visible in FIG. 4C is provided such that upon insertion of the plunger 114 into the device housing 110, the protrusion 126 is retained within the notch 123, in one non-limiting embodiment. The interface between the notch 123 and the protrusion 126 retains the disc member at the level of the notch 123 within the device housing 110. Upon proximal movement of the plunger 114, the proximal plunger 114 movement is limited by an interface between the disc member 124 and the stopper 116 on the plunger distal end. This interface limits the proximal movement of the plunger 114, and in some embodiments, prevents removal of the plunger 114 from the device housing 110.

In other embodiments described herein and shown in the FIGS, the disc member 124 is removably affixed or permanently affixed to the plunger rod in a predetermined position, wherein sliding of the plunger 114 within the device housing 110 moves the affixed disc member 124. When the plunger 114 is moved proximally such that the disc member 124 contacts the tabs 122 on the device housing 110, further proximal movement of the plunger 114 is prevented.

FIG. 5A provides a side view of the device embodiment 100 shown in FIG. 4, and FIGS. 5B-C provide cross-sectional views of the embodiment 100 shown in FIG. 5A at B-B. in FIG. 5, the plunger 114 of the device 100 has been inserted into the device 110, such that the disc member 124 has traversed the tabs 122, and is shown such that the protrusion 126 abuts the tab 122, limiting proximal movement of the plunger 114. The traversal of the disc member 124 is possible, as in some embodiments, the tabs 122 may be flexible and/or of a shape formed to allow the passage of the disc member 124 through the proximal end opening of the device, distally toward the distal end of the device 100. The shape of the tabs 122 may also serve to prevent or prohibit or deter proximal movement of the disc member 124 once inserted past the tabs 122 as shown in FIGS. 5A-C.

Figure 6:
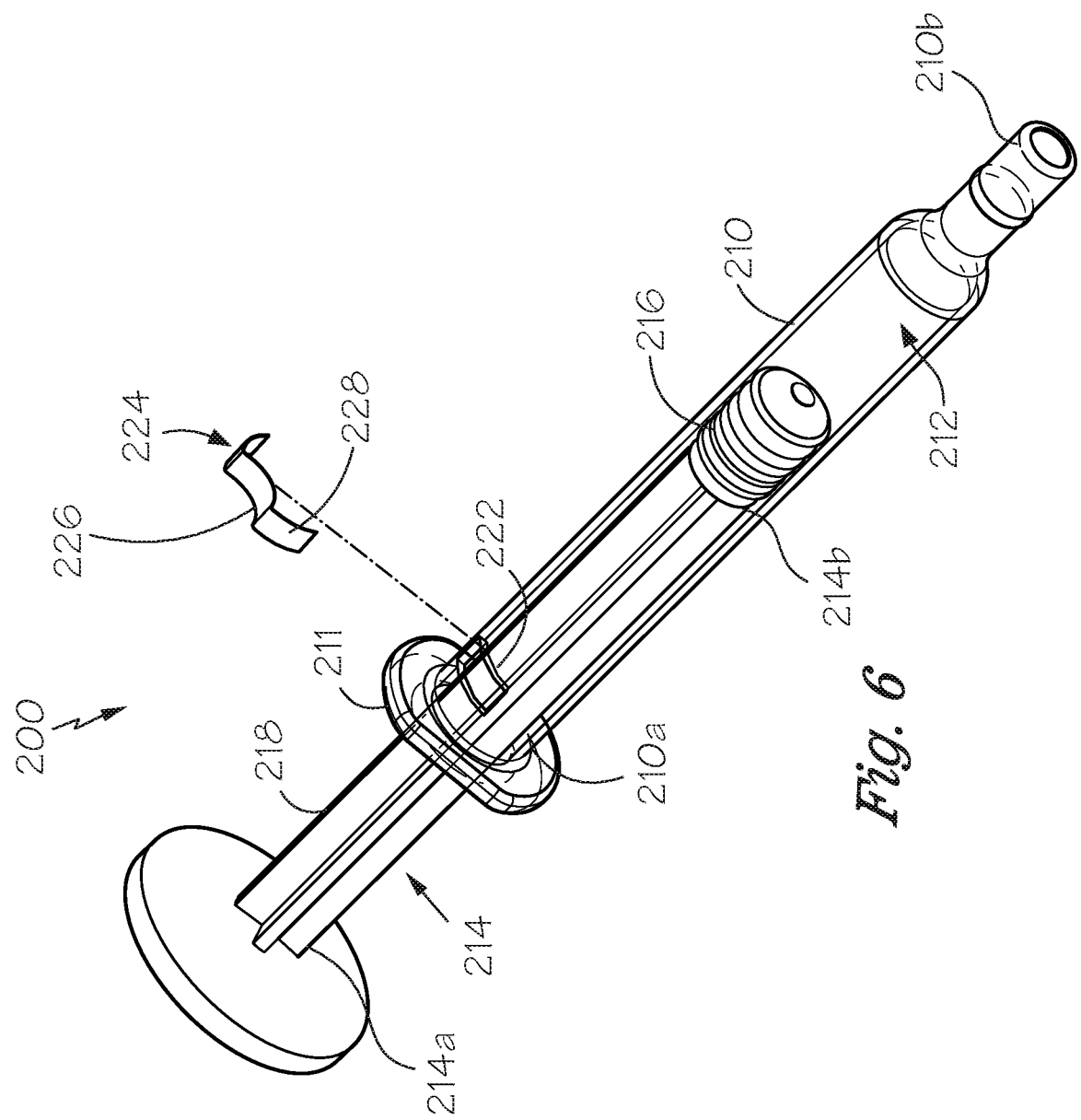
FIG. 6 is a perspective view of another embodiment of a medicament training device.

A further non-limiting embodiment 200 of the device is shown in a perspective view of FIG. 6. The device embodiment 200 includes a device housing 210 having a proximal end 210a and a distal end 210b, a housing flange 211 disposed near the proximal end 210a and a chamber 212 is provided there within, extending from the proximal end 210a to the distal end 210b for receiving at least a portion of a plunger 214 being slidable there within. The plunger 214 includes a proximal end 214a and a distal end 214b. The plunger 214 may optionally include a stopper 216 disposed thereon, near its distal plunger end 214b. In the embodiment shown in FIG. 6, the device housing 210 may include an opening 222 for receiving a portion of a catch member 224 for limiting movement of the plunger 214, in one particular embodiment, for limiting proximal movement of the plunger 214. The interaction between the catch member 224 and its interface with the plunger rod 214 via the opening 222 in the housing 210 provides a plunger limiting mechanism 220 (see FIG. 8). The catch member 224 may include a profile complimentary to the profile of a portion of the plunger rod 218, such that when a portion of the catch member 224 is received within the opening 222, the plunger 214 is movable in a proximal direction until the stopper 216 abuts the portion 226 of the catch member 224 protruding through the opening 222. In some embodiments, the catch member comprises a plunger interfacing portion 226, and a housing interfacing portion 228. The housing interfacing portion 228 of the catch member 224 may clip onto the outer surface of the device housing 210 to secure the catch member 224 to the device housing, in one non-limiting embodiment.

Figure 7:
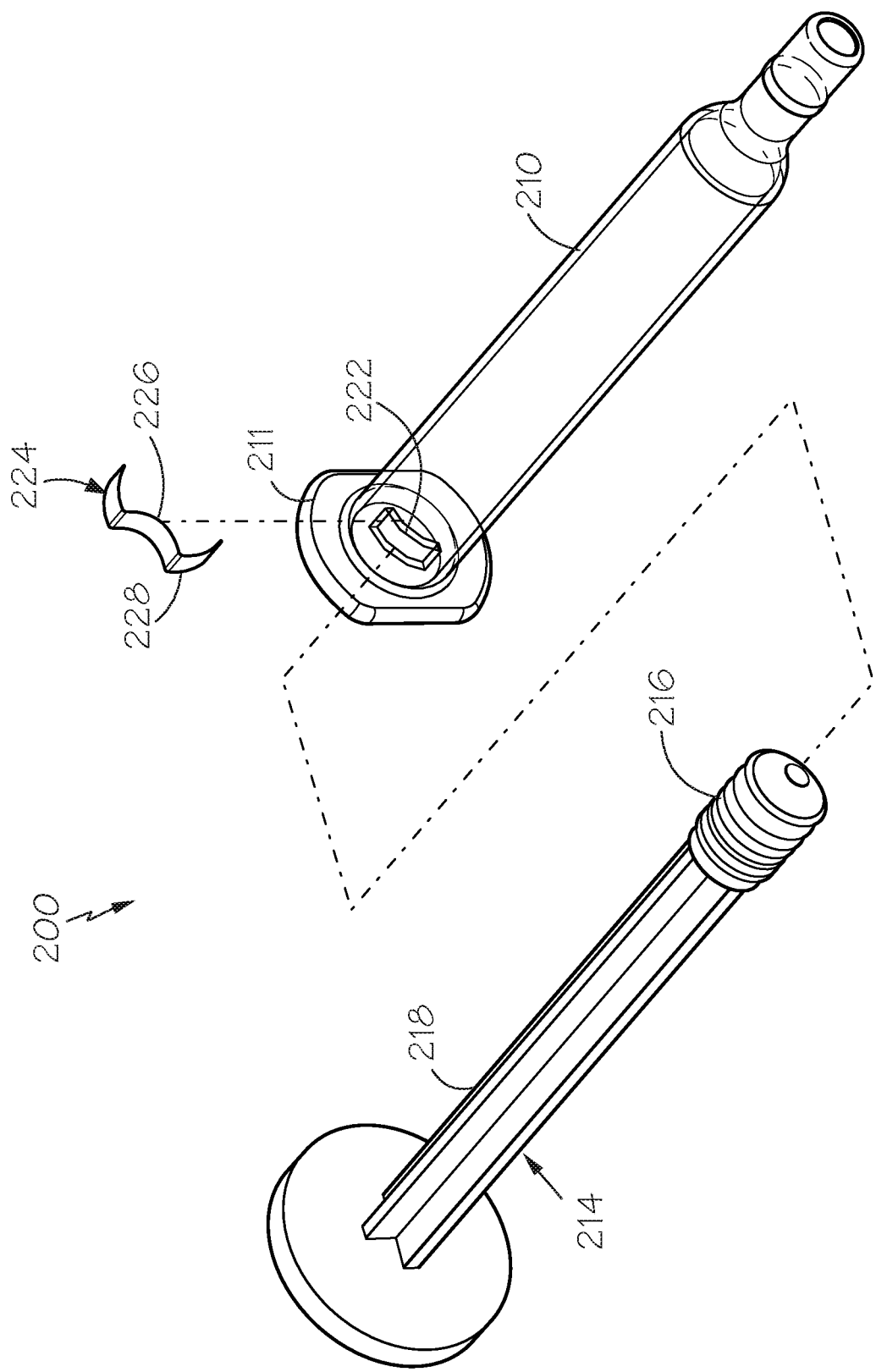
FIG. 7 is an exploded view of the embodiment of the device shown in FIG. 6.
Figure 8:
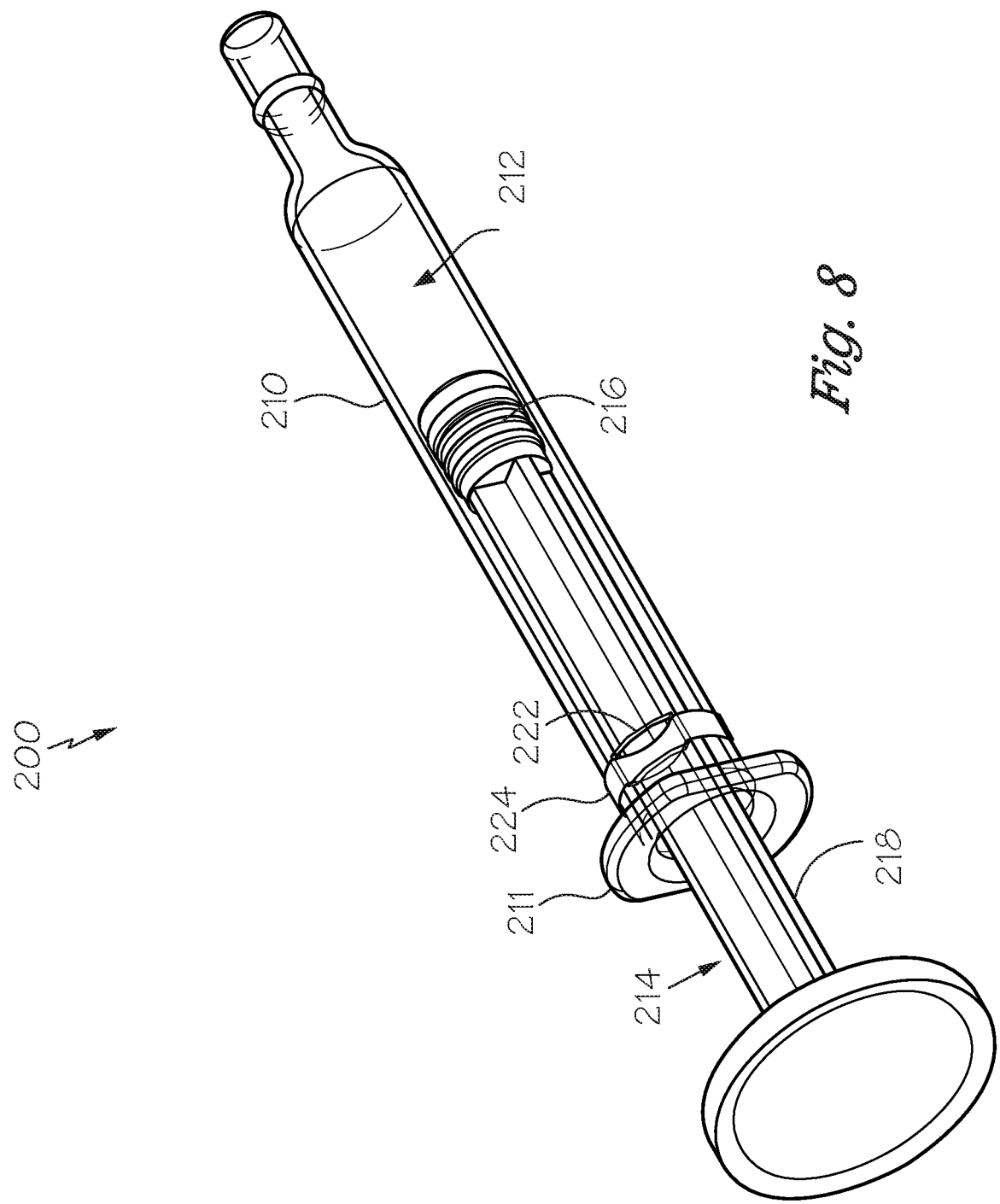
FIG. 8 is a rear perspective view of the embodiment of the device shown in FIG. 6, fully assembled, with the plunger rod distally disposed within the device housing.
Figure 9:
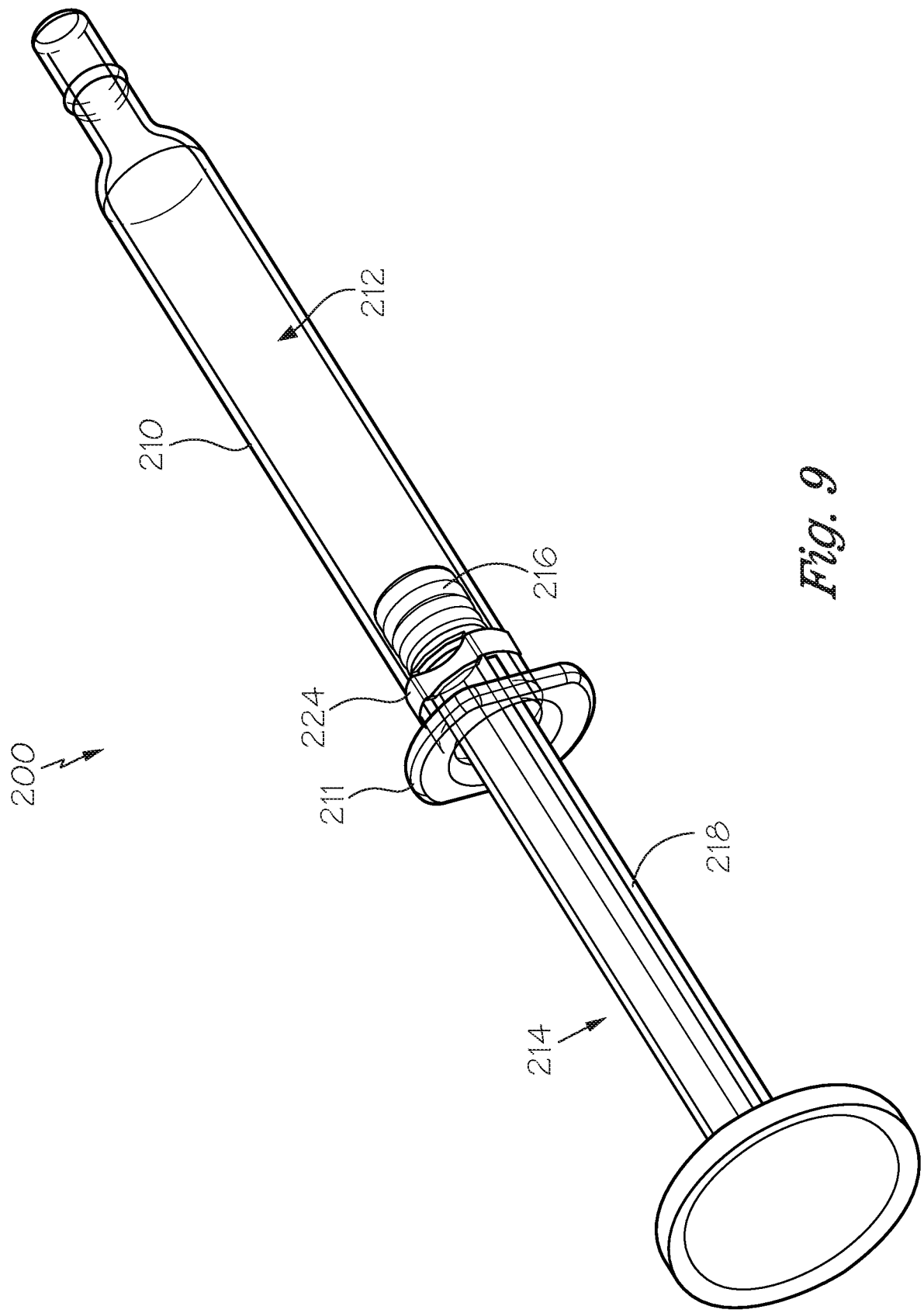
FIG. 9 is a rear perspective view of the embodiment of the device shown in FIG. 6, wherein the plunger is in a reset position.

FIG. 7 provides an exploded view of the device embodiment 200 shown in FIG. 6. FIG. 8 provides a rear perspective view of the device embodiment 200 shown in FIGS. 6-7, with the plunger two-thirds of the way into the chamber. FIG. 9 provides a rear perspective view of the device embodiment 200 as shown in FIG. 8, wherein the plunger 214 is moved in a proximal direction and the stopper 216 has abutted the catch member 224, preventing further proximal movement of the plunger 214 relative to the device housing 210. In other non-limiting embodiments, the opening 222 may be provided closer to the distal end of the device housing 210 to maintain the plunger 214 distal end toward the distal end of the housing 210. In other non-limiting embodiments, there may be multiple openings 222 along the length of the device housing 210 for limiting the proximal movement of the plunger 214, i.e. reset of the plunger 214, relative to the device housing 210. In some non-limiting embodiments, the openings 222 may be closeable with a membrane or a cap fitted to the dimensions of the opening. The varying positions of plunger 214 reset may depend on the medicament delivery device being simulated, or the type of medicament, or certain characteristics of the user training with the medicament training device 200. Therefore, in some non-limiting embodiments, the location at which the proximal movement of the plunger 214 is limited may be adjustable. The embodiment 200 of the device shown in FIGS. 6-9 provides a limitation on, or eliminates axial rotation of the plunger 214, in some non-limiting embodiments, by way of the plunger limiting mechanism 220 (i.e., the interface between the plunger rod 218 and the catch member 224).

Figure 10:
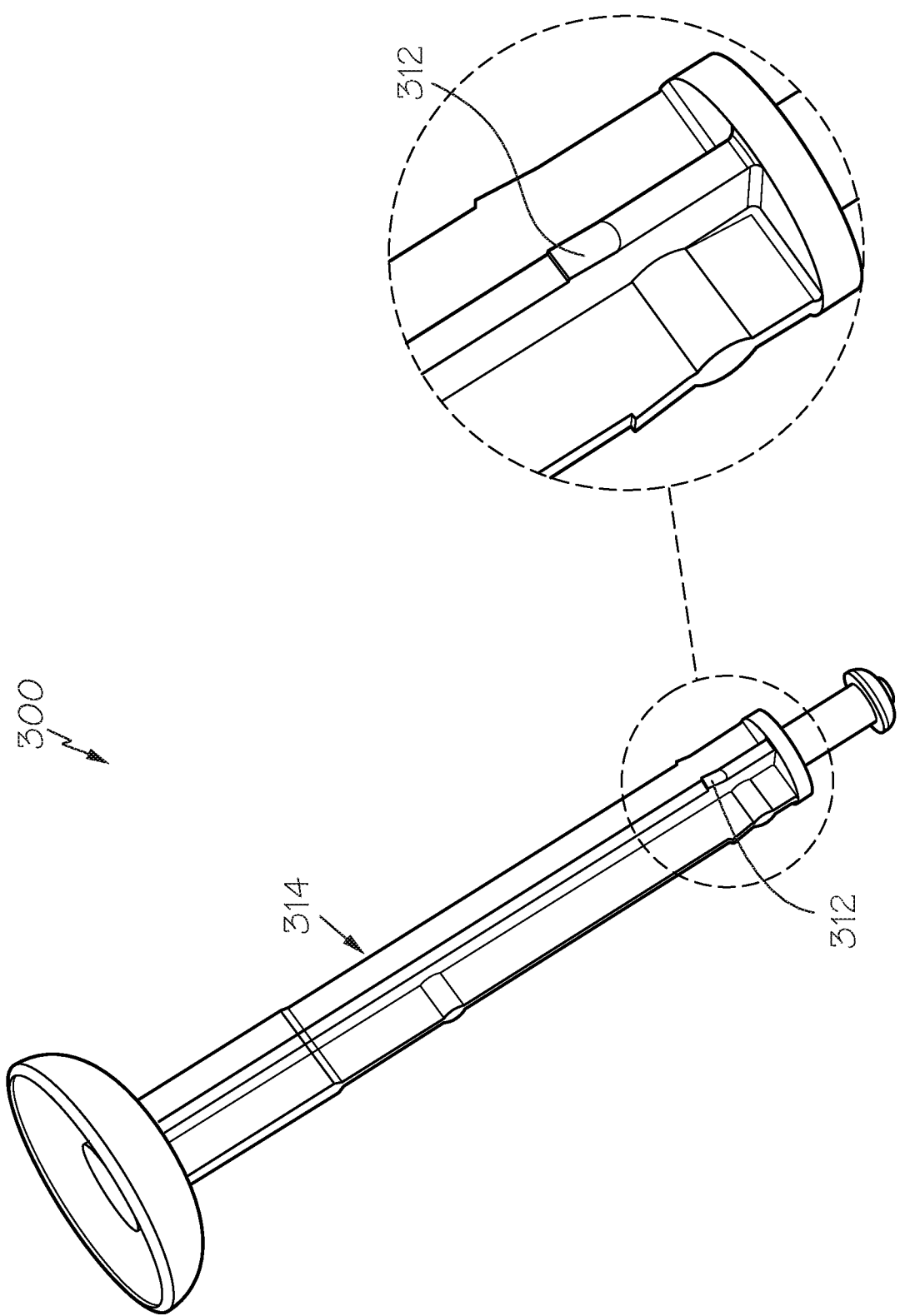
FIG. 10 is a perspective and zoomed in view of a plunger embodiment.
Figure 11:
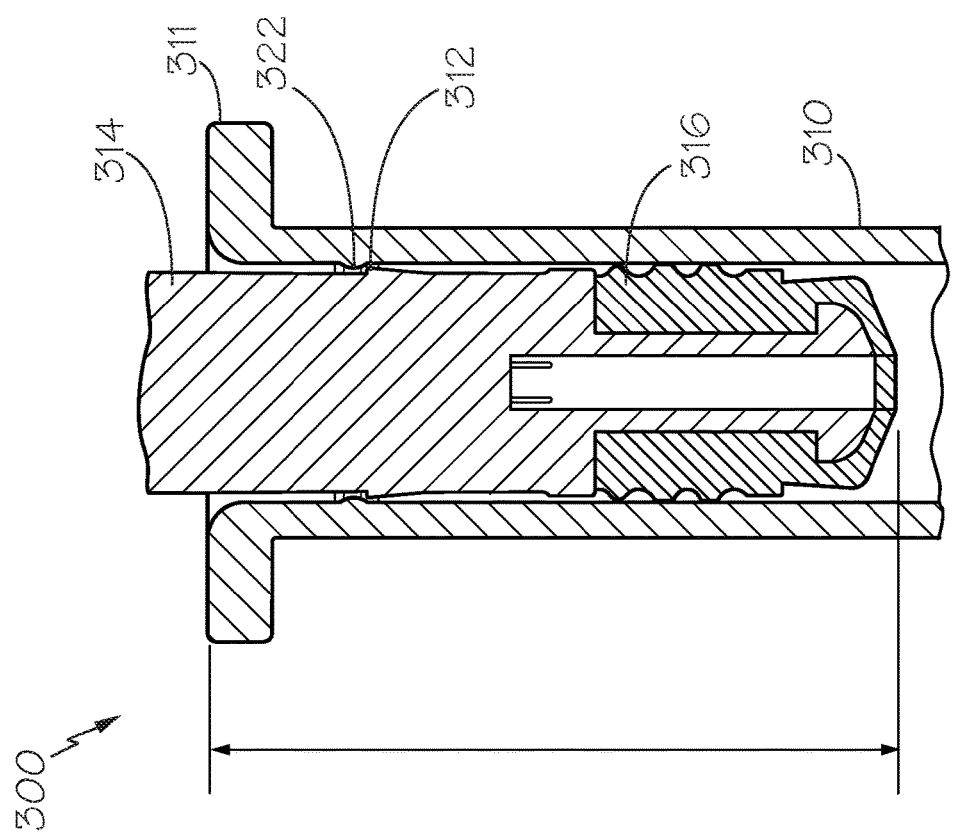
FIG. 11 is a cross sectional view of the plunger embodiment shown in FIG. 10 within a medicament training device embodiment housing.

FIG. 10 provides a perspective view of an embodiment 300 including a plunger 314 and a zoomed in view of a portion thereof, wherein the plunger 314 comprises a feature 312 for limiting proximal movement relative to the device housing 310 (housing shown in FIG. 11).

As can be seen in the partial cross-sectional view of FIG. 11, the device housing 310 includes a first interfacing component 322 and the plunger 314 comprises a second interfacing component 312 for interfacing with the first interfacing component 322 when the plunger is moved within the device housing 310 in a proximal direction. The second interfacing component may include a notch with a profile enabling insertion of the plunger into the device housing 310, but limiting proximal movement, i.e., limiting or preventing removal of the plunger 314 from the housing 310 once the second interfacing component 312 traverses the first interfacing component 322. For example, the profile of the notch may be smooth as the plunger is inserted and may include a rigid lower lip portion preventing removal of the plunger 314 due to the interface between the second interfacing component 312 and the notch 322 upon proximal plunger 314 movement.

In the embodiment 300 shown in FIG. 11, the first interfacing component 322 is provided on an inner surface of the housing 310. The first interfacing component 322 includes a nodule, in one embodiment, for interfacing with the notch 312, preventing removal of the plunger rod 314 from the device housing 310 by way of interaction between the notch 312 and the nodule 322. These interfacing component 312, 322 features may be positioned on the plunger rod 314 and housing 310, respectively, at any location to stop the plunger 314 proximal movement at any location desired, to train a patient to use the correct dosage of a particular medicament (i.e., to allow the plunger to reach the reset or refill line for example). In the partial cross-sectional view of the device embodiment 300 shown in FIG. 11, wherein the plunger 314 is received within the housing 310, the first interfacing component 322 prevents the plunger 312 from being removed from the housing 310. The device embodiment 300 also demonstrates the use of the device to train a user to reset the plunger 314 back to a reset or refill line position.

Similar to the catch member embodiment shown in FIGS. 6-8, FIG. 12A-D provides an alternative embodiment for a catch member, a clip 424, having one or more protrusions 426 on an inner surface thereof for interfacing with a plunger 418 of a device 400. The one or more protrusions 426 may traverse openings 422 in the housing 410 of the device shown in FIG. 12B, in one non-limiting embodiment. The housing 410 may include a housing flange 411 at or near its proximal end. The clip body 428, then surrounds a portion of the device housing 410 surface. Upon proximal movement of the plunger 414, the protrusions 426 contact the plunger rod 418, and may cause resistance during plunger 414 movement in some embodiments. The plunger 414 may also include a stopper 416 at its distal end. In some embodiments, the proximal movement of the plunger 414 may be limited by the interface between an upper portion of the stopper 416 and the clip 424, preventing removal of the plunger 414 from the device housing 410. In some non-limiting embodiments, the interface between the protrusions 426 and the plunger rod 418 limits or prevents axial rotation of the plunger 414. In some other examples, a disc member may be disposed between the plunger and the stopper or at the distal end of the plunger, at or near the stopper and the one or more protrusions 426 may interface with the disc member preventing removal of the plunger from the housing.

FIGS. 13A-C provide views of yet another embodiment of a clip 524 with a clip body 528 and a protrusion 526 having a pinching feature. The protrusion 526 may extend through an opening 522 (not shown) in the device housing 510 to contact the plunger rod 518, wherein upon movement of the plunger 514, resistance may be caused by the interface between the protrusion and the plunger rod 518 as seen in an embodiment 500 shown in FIGS. 13B-13C. Furthermore, proximal movement of the plunger 514 may be limited by the interaction between the clip 524 and the stopper 516 or a disc member disposed between the stopper and the distal end of the plunger 514. Plunger 514 removal from the device housing 510 may be prevented in this manner. Axial rotation of the plunger 514 is limited or prevented by the interface between the protrusion 526 and the plunger rod 518.

FIGS. 14A-D includes yet another embodiment in which a device embodiment 600 includes a plunger 614, movable within a chamber 612 of a device housing 610. The device housing 610 includes a proximal end 610a and a distal end 610b, and a flange 611 at or near its proximal end 610a. The plunger 614 may include a cylindrical shaped plunger rod 618, in a non-limiting embodiment, and a stopper 616 at or near its distal end. The flange 611 may include or be associated with an annular member 609, which in some examples may include a toroidal or cannulated spring, an o-ring, or other annular device. The annular member 609 may be formed as part of the flange 611 or be associated therewith. In other embodiments, the annular member 609 may be formed as part of the housing 610, and/or the housing 610 may include a pocket for receiving the annular member 609 on an inner surface thereof. Upon assembly of the device 600, the annular member 609 and flange 611 are placed on the plunger rod 618 or at the proximal end of the device housing 610, for example, such that during movement of the plunger 614 in the proximal direction the stopper 616 abuts a portion of the flange 611, for example, a lower surface of the flange 607 within the chamber 612, preventing removal of the plunger 614 from the device housing 610. In some embodiments, the pocket 613 may be provided either on the plunger rod 618 or in the flange 611 as shown in FIG. 14B, or even in the device housing 610 for resting of the annular member 609. The annular member 609 also provides a resistance mechanism to confer resistance to the plunger 614 during movement of the plunger relative to the housing 610. This feature may be used to simulate injection device function for training purposes. In some non-limiting embodiments, resistance may be greater during distal movement of the plunger (movement toward the distal end of the device housing 610b), and lesser during plunger reset (i.e., during proximal plunger movement). The proximal plunger movement may also be restricted or limited at different points along the device, for example, at a predetermined reset or refill line, in order to mimic or simulate the reset or refill line reset of an injection device.

Figure 15B:
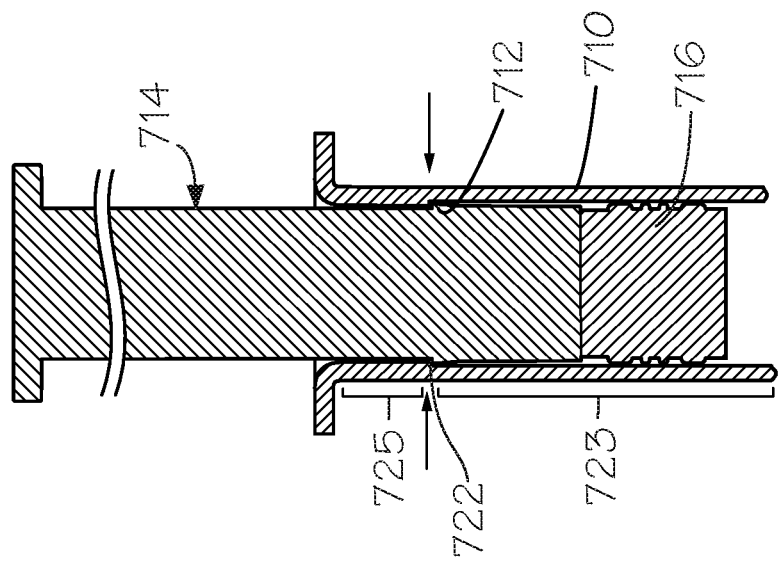
FIG. 15B provides a cross sectional view of a device embodiment including the plunger embodiment of FIG. 15A.
Figure 15A:
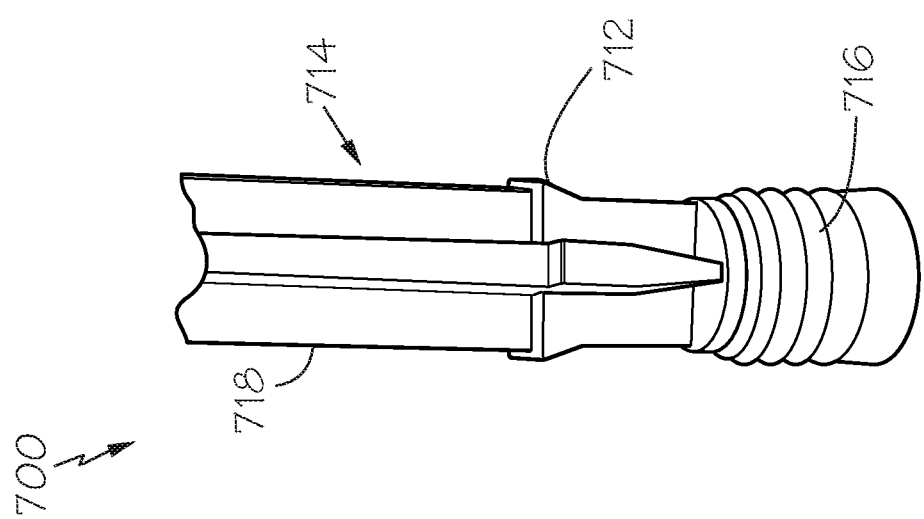
FIG. 15A includes a perspective view of a distal end of a plunger embodiment.

FIG. 15A is a partial perspective view of a distal end of a plunger 714 embodiment. The plunger includes a plunger rod 718, and a protrusion 712 on a portion thereof. The plunger 714 is associated with a stopper 716. FIG. 15B includes a cross-sectional view of the plunger 714 disposed within a device housing 710. In the device embodiment 700 shown in FIG. 15B, a variation in the thickness of the device housing 710 wall is shown. A first portion 725 of the device housing 710 includes a smaller inner diameter than a second portion 723 of the device housing 710, such that a tab 722 is formed in the device housing 710 wall at the intersection between the first portion 725 and the second portion 723. The intersection, therefore, forms a tab 722, configured to abut the protrusion 712 on the plunger when the plunger is moved proximally within the device housing 710. This interaction of components prevents the plunger from being removed from the device, and further, stops the proximal plunger movement at a predetermined point within the device housing 710.

FIG. 16A includes a cross-sectional view of a further device embodiment 800 including a plunger 814 having a plunger rod 818, the plunger rod 818 including a cross-shaped profile. At a position on the plunger rod 818 between the proximal and distal ends of the plunger rod 818, there may be a disc member 824. The disc member 824 may be provided at the distal end of the plunger rod 818 as shown in the embodiment in FIG. 16A, for example. The device 800 may further include a housing 810, having multiple inner housing tabs 822 extending into the chamber of the housing 810. There may be at least one tab 822 in an embodiment. In another embodiment, two tabs 822 may be provided. In at least another embodiment, three tabs 822 may extend into the chamber, and in a further nonlimiting embodiment, the tabs 822 may be spaced 120 degrees from one another. In yet a further nonlimiting embodiment, as shown in the cross-sectional view in FIG. 16B, four inner housing tabs 822 may extend into the chamber of the housing 810. These inner housing tabs 822 are configured to limit proximal movement of the plunger 814 by interfacing with the disc member 824 on the plunger rod 818 when the plunger rod 818 is moved proximally within the device housing 810. In some instances, the device embodiment 800 may limit rotational movement of the plunger rod 818 due to an interface between the plunger rod 818 and the inner housing tabs 822. Whether the rotational movement of the plunger rod 818 is limited by the tabs 822 in this embodiment depends on the dimensions of the tabs 822 and the plunger rod 818.

Figure 17A:
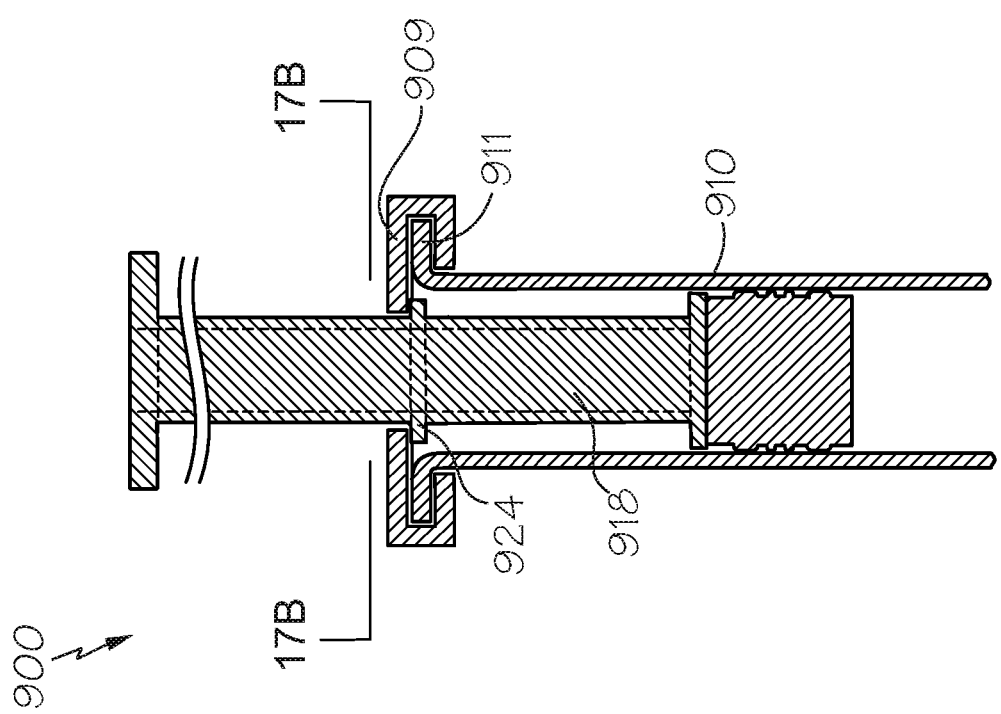
FIG. 17A is a cross sectional view of a device embodiment.
Figure 17B:
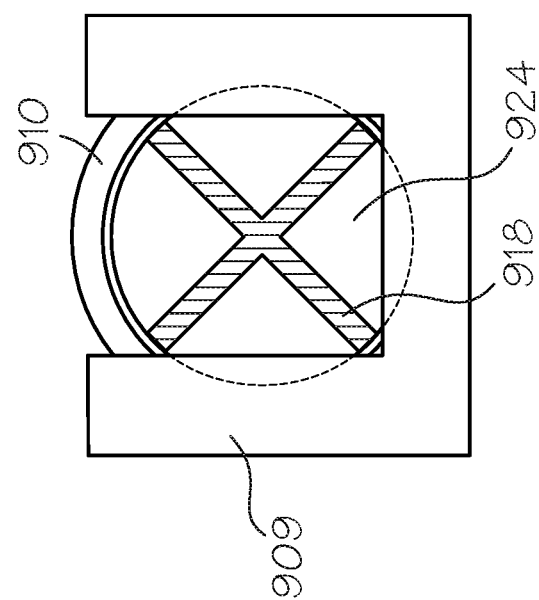
FIG. 17B is a cross-section of the device embodiment shown in FIG. 17A.

In yet another embodiment, a device 900 is provided in FIGS. 17A-17B. FIG. 17A includes a cross-sectional view of an embodiment 900 including a device housing 910 forming a chamber there within, a plunger having a plunger rod 918 slidable there within, and a plunger limiting mechanism. The plunger limiting mechanism comprises a disc member 924, disposed on the plunger rod 918, between its proximal and distal end, and an extended flange component 909. The extended flange component 909 can be removably or permanently attached to the flange 911 of the device 900, in one example. The extended flange component 909 is configured to abut the disc member 924 on the plunger rod 918 to limit proximal movement of the plunger rod 918 relative to the housing 910 as shown in FIG. 17A. In the cross-sectional view of FIG. 17B, the device housing 910 is partially visible beneath the extended flange component 909, which is abutting the disc member 924, preventing further proximal movement of the plunger rod 918. The disc member 924 may be located on the plunger rod 918 at a location wherein the reset or refill line is set, so that plunger may only be proximally moved within the housing 910 a pre-set distance, wherein the pre-set distance may correlate to a position of a medicament-containing injection device to simulate an effective dose. An effective dose, as aforementioned, may be based on patient dosing regimen, drug dosage requirements, concentration or strength of the medication, particular disease or disorder to be treated, among other criteria. This feature assists in training an individual to only move the plunger proximally to the reset or refill line to obtain the effective dose. Moreover, rotational movement of the plunger rod 918 relative to the extended flange component 909 is limited, or in some instances prevented, due to the interface between the cross members of the plunger rod 918 and the extended flange component 909.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. An injection device, comprising:
   a housing comprising an outer surface, an inner surface, a proximal end and a distal end, and an opening extending there between, the housing comprising at least one first interfacing component in its inner surface, said first interfacing component comprising a notch;
   a plunger rod having a first end and a second end, and a stopper disposed at its distal end the plunger being movable within the opening of the housing, the plunger rod comprising a plunger rod profile and at least one second interfacing component on its outer surface comprising a disc member, said disc member comprising a protrusion for interfacing with the notch and a disc member opening for receiving the plunger rod, the opening of the disc member comprising a profile for interfacing with the plunger rod profile to prevent rotation of the disc member relative to the plunger rod, wherein said plunger rod is movable relative to the disc member;
   wherein the at least one notch interfaces with the at least one disc member protrusion to limit proximal plunger rod movement;
   wherein proximal plunger rod movement in the opening is limited by contact between the stopper and the disc member.

2. The injection device of claim 1, wherein the housing comprises a flange adjacent to the proximal end of the housing.

3. An injection device, comprising:
   a housing comprising an outer surface, an inner surface, a proximal end and a distal end, and defining a chamber extending between the proximal end and the distal end;

a plunger having a first end and a second end, the plunger being movable proximally and distally within the chamber of the housing, the plunger comprising a plunger rod extending from the first end to the second end of the plunger, the plunger rod comprising a plunger rod profile; and a plunger limiting mechanism configured to limit the proximal movement of the plunger at a location of the housing, wherein the plunger limiting mechanism comprises at least one tab and a disc member, the at least one tab extending from the inner surface of the housing, and the disc member disposed on a portion of the plunger rod, said disc member comprising an opening for receiving the plunger rod, the opening of the disc member comprising a profile for interfacing with the plunger rod profile to prevent rotation of the disc member relative to the plunger rod;

wherein an interface between the disc member and the at least one tab limits proximal movement of the plunger.

4. A method of resetting a plunger, comprising:

obtaining the device of claim 3; and moving the plunger in a proximal direction until the plunger limiting mechanism impedes further proximal movement of the plunger.

* * * * *